US00PP31652P3

(12) United States Plant Patent
Maillard et al.

(10) Patent No.: US PP31,652 P3
(45) Date of Patent: Apr. 14, 2020

(54) PEACH TREE NAMED 'PBRO15170'

(50) Latin Name: ***Prunus persica* (L.) Batsch**
Varietal Denomination: PBRO15170

(71) Applicant: AGRO SELECTIONS FRUITS, Elne (FR)

(72) Inventors: Arsène Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 16/350,456

(22) Filed: Nov. 20, 2018

(65) Prior Publication Data

US 2019/0159390 P1 May 23, 2019

(30) Foreign Application Priority Data

Nov. 23, 2017 (QZ) ..... PBR 2017/3051

(51) Int. Cl.
*A01H 5/08* (2018.01)
*A01H 6/74* (2018.01)

(52) U.S. Cl.
USPC ..... Plt./195
CPC ..... *A01H 6/7463* (2018.05)

(58) Field of Classification Search
USPC ..... Plt./195
See application file for complete search history.

*Primary Examiner* — Anne Marie Grunberg
(74) *Attorney, Agent, or Firm* — Birch, Stewart, Kolasch & Birch, LLP

(57) ABSTRACT

A new and distinct variety of white peach tree denominated 'PBRO15170' is resistant to main pests and diseases, and has fruits with high eating quality and very long shelf life without alteration before and after harvesting, with a semi-sweet white flesh, with a red pigmentation into the stone cavity and around the cavity, and an attractive luminous and homogenous skin with a high percentage of purple red blush on skin surface, on a pink red background.

3 Drawing Sheets

Botanical classification: *Prunus persica* (L.) Batsch.
Variety denomination: 'PBRO15170'.

This application claims priority of Community plant variety right No. 2017/3051 filed on Nov. 23, 2017 (Nov. 23, 2017.) which is hereby incorporated by reference in its entirety.

BACKGROUND OF THE NEW VARIETY

The present invention relates to a new and distinct variety of white peach tree, *Prunus persica* (L.) Batsch, which has been given the variety denomination 'PBRO15170'.

This new tree produces fruits with a long shelf life without alteration both on the tree after growth completion and after harvesting, very good eating quality, clingstone white flesh fruits with a red pigmentation around the stone cavity, for fresh market in August in the Pyrénées-Orientales department, France.

ORIGIN OF THE VARIETY

The 'PBRO15170' white peach tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'PBRO15170' from an open pollination of the white peach tree variety named 'SWEETSTAR' (U.S. Plant Pat. No. 21,145), which was used as the seed parent. Thus, the pollen parent remains unknown.

The 'PBRO15170' variety was obtained by hybridizing and propagated by grafting on a "INRA® GF677" rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'PBRO15170' white peach tree blooms generally during March near Elne in the Pyrénées-Orientales department, France. More particularly, the beginning of the blooming period occurs generally March 9$^{th}$. The blooming period is considered medium. However, it was observed that its early date of blooming seems to be highly dependant on climatic conditions.

The first fruit of 'PBRO15170' ripens generally at the beginning of August. More particularly, the beginning of the ripening period occurs between July 30$^{th}$ and August 2$^{nd}$. However, it was observed that its early date of maturity seems to be highly dependent on climatic conditions.

DESCRIPTION OF THE DRAWINGS

In the accompanying drawing, which are as nearly true as it is reasonably possible to make in a color illustration of this type.

Figure 1:
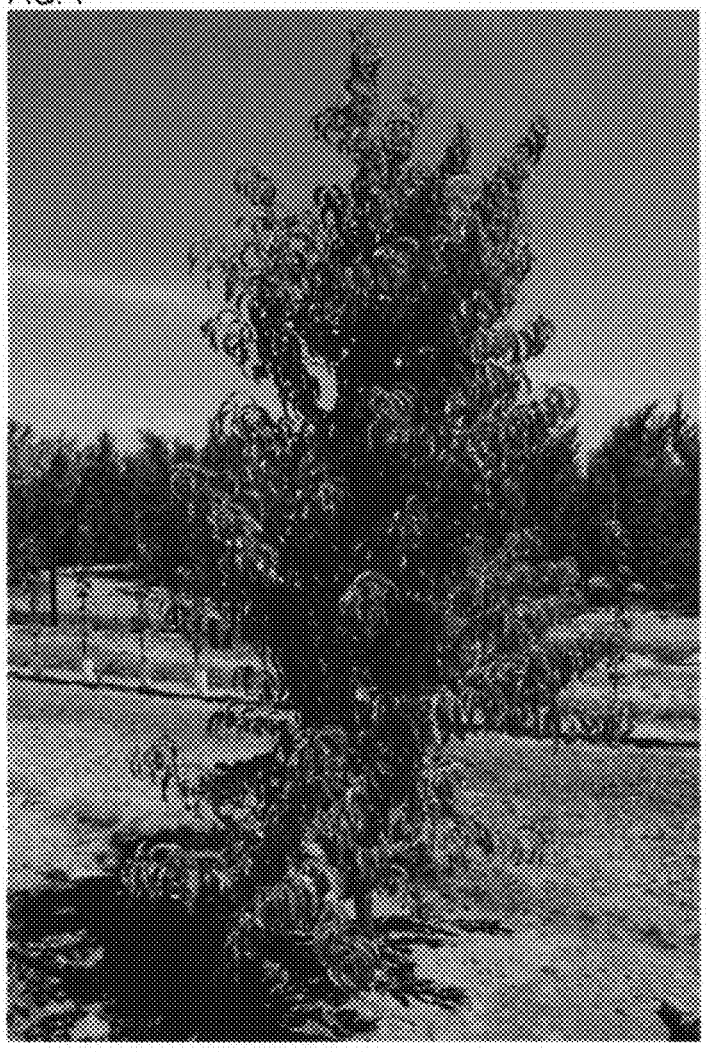
FIG. 1 is a color photograph that shows a typical specimen of a tree of the new variety 'PBRO15170' in orchard, with branches bearing fruits.
Figure 2:
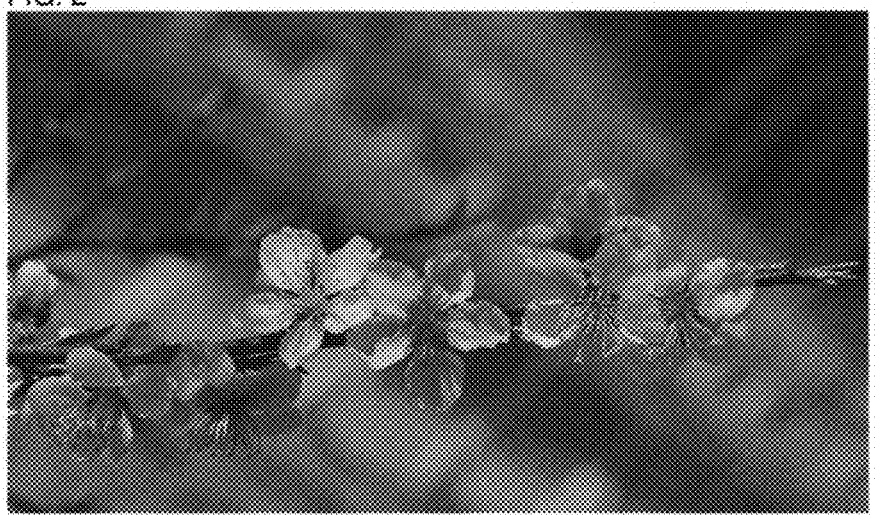
FIG. 2 is a color photograph which shows a branch of a tree of the new variety 'PBRO15170' in orchard bearing flowers at blossoming time.
Figure 3:
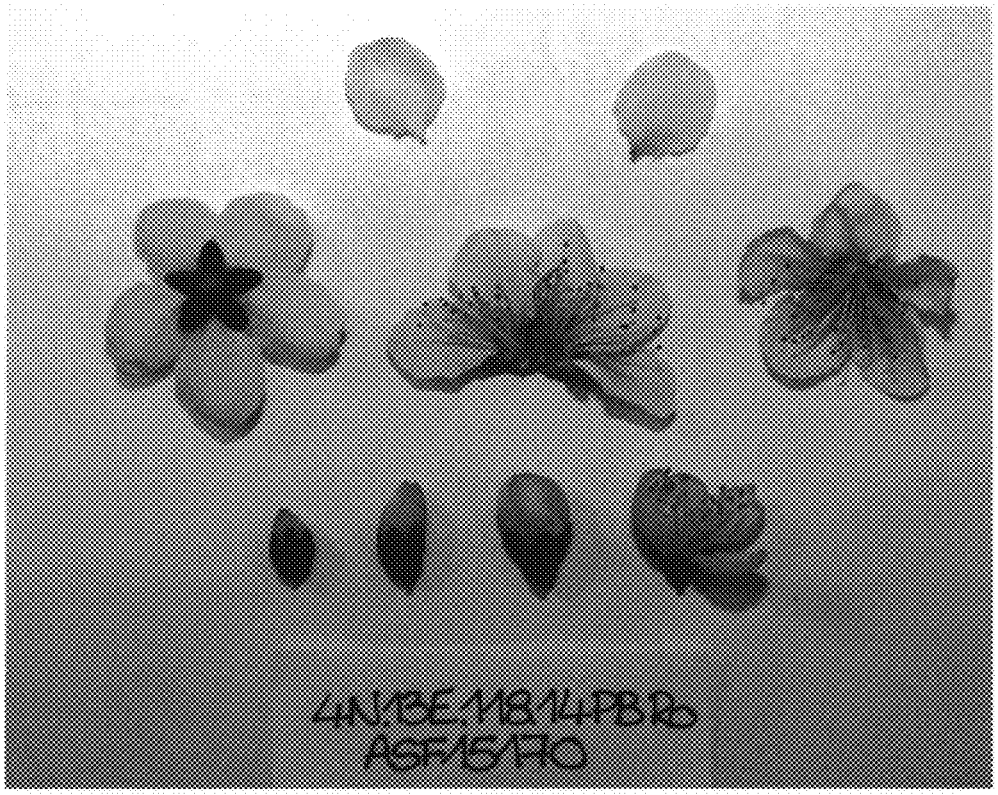
FIG. 3 is a color photograph which depicts the flower buds at different development stages, and the reverse and side view of the flower and the reproductive organs with petals removed, of the new variety.
Figure 4:
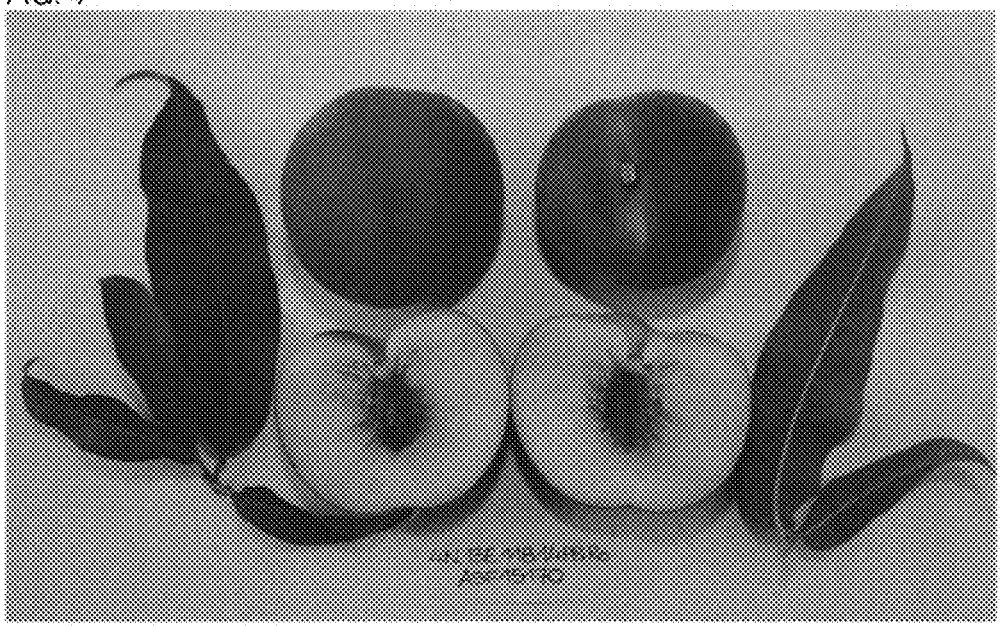
FIG. 4 is a color photograph which shows the upper and lower sides of leaves and three typical specimens of the fruit, one having been cut in half with the stone being left in one of the halves for depicting leaves, fruit flesh, the stone and the stone cavity of the new variety.
Figure 5:
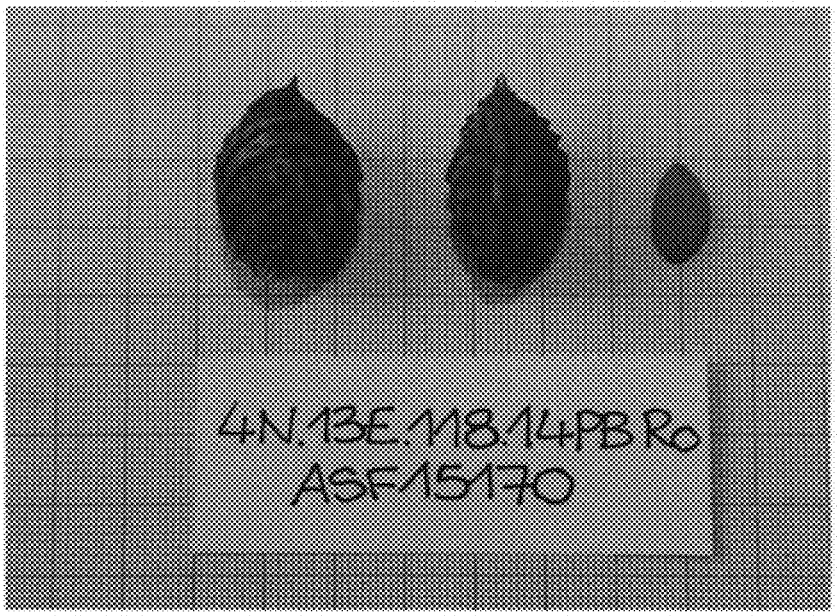
FIG. 5 is a color photograph showing different views of the stone of the new variety and the kernel of the stone.

The enclosed photographs show plants in their third growing season for trees and flowers and plants in their second growing season for leaves, fruits and stone. Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'PBRO15170' is high, due to fruit very long shelf life without alteration after harvesting.

Trees are medium vigorous and large stature half-standing in a semi-flared aspect. The time of beginning of flowering is considered medium; flowering begins at the beginning of March. The type of flower is showy (rosette) with medium to large petal size. Petals are light pink to pink. Leaf glands are present and reniform. The fruit flesh is white generally with a red pigmentation into the stone cavity and around the stone cavity. The fruit skin is medium thick, with a luminous and homogenous purple red blush on a washed red or pinkish red background. The stone is clingstone and his size is medium for the variety. Fruit taste is semi-sweet, very aromatic and with a high level of sugars.

Compared to 'SWEETSTAR' variety (U.S. Plant Pat. No. 21,145), which is the seed parent of the new variety, the fruits of 'PBRO15170' variety ripen usually 10 days earlier. Moreover, the new variety 'PBRO15170' is less sensitive, almost resistant, to disease such as powdery mildew. The two varieties 'PBRO15170' and 'SWEETSTAR' are quite similar in terms of size and fruit shape. However, the fruits produced by the new variety 'PBRO15170' show a purple red color whereas the fruits of the variety named 'SWEETSTAR' are colored in a pink red.

Compared to 'MAPERLA cov ASF0363' white peach tree (not patented), the fruits of the new variety 'PBRO15170' ripen later. More particularly, the fruits of the variety 'PBRO15170' ripen 5 to 10 days later than the fruits of 'MAPERLA cov ASF0363'. The fruits of 'MAPERLA cov ASF0363' have an equilibrate flavor, i.e. mode acid, than the fruit taste of the new variety 'PBRO15170', which is considered to be semi-sweet, sugary and aromatic. The fruits produced by the new variety 'PBRO15170' are larger than the fruits of the similar variety 'MAPERLA cov ASF0363'.

Compared to 'SWEETALY cov ASF1151' white peach tree (not patented), which produced fruits that become mature in the middle of June, the fruits of the variety new variety 'PBRO15170' ripen later, typically in the middle of August. The fruits produced by the new variety 'PBRO15170' are larger than the fruits of the similar variety 'SWEETALY cov ASF1151'.

DETAILED DESCRIPTION

Referring more specifically to the pomological details of this new and distinct variety of white peach tree, the following was observed on trees in their third growing season (second year of production) for trees, trunk and flowers, excepted on trees in their second growing season (first year of production) for leaves, fruits and stones. The characteristics were observed under the ecological conditions prevailing at the orchards located near the town of Elne, Pyrénées-Orientales departement, France. All observations have been done on rootstock cultivars. Used rootstocks were "INRA® GF677" trees. All major color code designations are by reference to The R.H.S. (Royal Horticultural Society) Colour Chart (Fourth Edition) provided by The Royal Horticultural Society of Great Britain.

Tree:

*Size.*—

*Generally.*—Considered large. The tree size the first year was approximately 200 to 280 cm. The tree was pruned during each following dormant season to a height of approximately 250 cm. Current season shoots growth could reach 80 cm. The tree size from the second year (second and next years) reached a final height of 330 cm including current season shoots length. The tree size is consistently reduced to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered medium to strong.

*Productivity.*—Very Productive and regular, every year. Fruit set is spaced by thinning to develop the remaining fruit into the desired market sized fruit. The number of the fruit set varies with the prevailing climatic conditions and cultural practices employed during the bloom period and is therefore not distinctive of the present variety.

*Bearer.*—Very regular. The fruit distribution is considered homogenous on mixed branches and spurs having more than 1 year. Thinning should be reduced or very reduced because of the capacity of the tree to produce homogeneous fruits with a high potential.

*Form*.—The 'PBRO15170' variety has naturally a semi-flared shape.

*Density*.—Considered dense.

*Hardiness*.—The present tree was grown and evaluated in France. The variety appears to be hardy under the central Pyrénées-Orientales departement typical climatic conditions. Experimentations on the same orchard in Elne, Pyrénées-Orienteles department, with winter chilling requirement below 7.2° C. comprised between 350 hours and 1200 hours according to the specificities of the year, namely 1076 hours in 2012-2013, 767 hours in 2013-2014, 552 hours in 2014-2015, 721 hours in 2015-2016, and 784 hours in 2016-2017 showed a good behavior of the tree in all cases. No damages were caused by ascertained temperatures as low as −12 degrees Celsius in winter. The tree was also very resistant to frosty springtime weather.

Trunk:

*Diameter*.—Approximately 72.0 to 80.0 millimeters in diameter when measured at approximately 20 centimeters above the soil level during the 3$^{rd}$ growing season.

*Bark texture*.—Considered rough, with lenticels.

*Lenticels*.—Numerous lenticels are present. The number of lenticels reaches 3 lenticels per cm$^2$. The lenticels range in size from approximately 1.5 to 2.0 millimeters in width, and about 5.0 to 8.0 millimeters in height.

*Lenticel color*.—The lenticels have a light orange color (RHS Greyed Orange 165 B to RHS Greyed Orange 165 C).

*Bark coloration*.—The bark has a brown color (RHS Greyed Orange 165 A) slightly darker than the lenticel color.

Branches:

*Size*.—Mature branches and current season shoots are considered medium for the variety.

*Diameter*.—Average as compared to other peach varieties. The current season shoots have a diameter of about 4.0 to 6.0 millimeters, and mature branches have a diameter of about 8.0 to 10.0 millimeters.

*Surface texture*.—Smooth for current season shoots and rough, with lenticels, for mature branches. Wood which is several years old has no furrowed appearance.

*Crotch angles*.—Primary branches are considered variable, but the crotch angles are generally of 60 degrees from the horizontal axis for current season shoots and for mature branches. This particular characteristic is not considered distinctive of the variety, however.

*Current season shoots*.—

*Internode length*.—Generally between 20.0 and 27.0 millimeters.

*Color*.—The color of new shoot tips is considered light green (RHS Yellow Green 145 A) on lower part of new shoot tips, whereas the upper part is darker and colored in purple (RHS Greyed Red 178 A to RHS Greyed Red 178 B), depending on the level on the tip.

*Mature branches*.—

*Internode length*.—Generally between 24.0 and 32.0 millimeters.

*Color of mature branches*.—Brown (RHS Grey Brown 199 A).

*Lenticels*.—Numerous small lenticels are present on mature branches. The number of lenticels reaches 4 lenticels per cm$^2$. The lenticels range in size approximately 0.5 to 1.0 millimeter in width, and about 1.5 to 2.0 millimeters in height and about 1.0 to 1.5 millimeters in diameter.

*Lenticel shape*.—Round stretched.

*Lenticel color*.—The lenticels have a beige color (RHS Greyed Orange 164 C to RHS Greyed Orange 164 D).

Leaves:

*Size*.—Considered medium to large for the species.

*Leaf length*.—Approximately 184.75 millimeters with leaf petiole.

*Leaf width*.—Approximately 44.75 millimeters.

*Leaf base shape*.—Round.

*Leaf form*.—Entire.

*Leaf tip form*.—Caudate.

*Leaf color*.—

*Upper leaf surface*.—Dark Green (RHS Green 137 B).

*Lower surface*.—A lighter green (RHS Yellow Green 147 B) than the upper leaf surface color.

*Leaf texture*.—Both surfaces of the leaves are smooth and glabrous.

*Leaf venation*.—Pinnately veined.

*Mid-vein*.—

*Color*.—Light green, almost cream white (RHS Yellow Green 145 D). The color may evolve with maturity.

*Thickness*.—Approximately 1.5 millimeters.

*Lateral veins*.—

*Color*.—The lateral veins are considered a light green (RHS Yellow Green 145 C).

*Leaf margins*.—

*Form*.—Considered crenate.

*Uniformity*.—Leaves are isolated or grouped by 2 or 3. In this last case, one leaf of normal size is found with one or two smaller leaves (at least 50% smaller).

*Leaf petioles*.—

*Size*.—Considered medium.

*Shape*.—Ribbed.

*Length*.—About 9.0 to about 11.0 millimeters.

*Diameter*.—About 1.5 to 2.0 millimeters.

*Petioles color*.—

*Upper petiole surface*.—Light green (RHS Yellow Green 145 A).

*Lower surface*.—Light green (RHS Yellow Green 145 B).

*Ratio between limb length and petiole length*.—18.

*Leaf glands*.—

*Size*.—Considered small. Their size is about 2.0 millimeters in length and 1.5 millimeters in width.

*Number*.—Generally 2 glands per leaf, sometimes 3 glands.

*Type*.—Reniform.

*Position*.—The leaf glands are on alternate position on the upper part of the petiole.

*Color*.—On young leaves, leaf glands color is considered a light green (RHS Yellow Green 145 B). On older leaves, leaf glands color turns to a dark brown (RHS Brown 200 A to RHS Brown 200 B).

*Leaf stipules.*—

*Generally.*—No leaf stipules were observed. But as seen in the characteristic relative to the leaves uniformity, it is possible to find leaves by groups of 2 or 3, with a normal-size leaf and smaller ones.

Flowers:

*Flower buds.*—

*Generally.*—At pre-floral stage of development, the floral buds are conic shaped. Their form is evolving until blooming, with variables dimensions. Just before blooming, floral buds are approximately 9.0 to 10.0 millimeters wide and approximately 19.0 to 20.0 millimeters long. The distribution of the flower buds is considered homogenous on the trees.

*Color.*—This characteristic is dependent upon the proximity to bloom. At pre-floral stage of development (stage A), the bottom of the flowers buds, or calyx, or flower receptacle, formed by the sepals, is of purple-brown color (RHS Greyed Purple 187 A or RHS Greyed Purple 187 B) on its outer face. The inner surface of the calyx is considered orange yellow (RHS Yellow Orange 21 A). The corolla, formed by the petals, is generally of medium pink color (RHS Red Purple 65 A to RHS Red Purple 65 B). Petals color shows an evolution until the end of flowering.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—The blooming time generally begins during the first two weeks of March. The first bloom was observed on 2016.

*Blooming time.*—Considered medium in relative comparison to other commercial peach cultivars grown in the Pyrénées-Orientales departement, France. The date of full bloom is observed generally at the middle of the blooming period. The date of bloom varies slightly with climatic conditions and cultural practices. Thus, the full bloom was observed from Mar. 9 until Mar. 17, 2016, then from Mar. 9 until Mar. 16, 2017 and then from Mar. 7 until Mar. 14, 2018.

*Duration of bloom.*—Approximately 8 to 9 days. This characteristic varies slightly with the prevailing climatic conditions.

*Flower type.*—The variety is considered to have a showy type flower (rosette).

*Flower size.*—Considered medium to large. Flower diameter at full bloom is approximately 41.0 to 44.0 millimeters.

*Bloom quantity.*—Considered very abundant, approximately between 40 and 45 flowers per meter, with a good distribution and a high rate of fruit set.

*Flower bud frequency.*—Generally 2 flower buds appear per node, occasionally 1.

*Petal size.*—

*Generally.*—Considered medium to large.

*Length.*—Generally 22.0 to 23.0 millimeters.

*Width.*—Generally 18.0 to 19.0 millimeters.

*Petal form.*—Round-shaped.

*Petal count.*—Generally 5.

*Petal texture.*—Both surfaces of the petals are smooth, glabrous and soft.

*Petal color.*—Both surfaces of the petal are colored with a pale pink to pink (RHS Red Purple 65 B) when young, becoming slightly darker until the end of blooming.

*Petal arrangement.*—Slightly overlapping.

*Fragrance.*—Sweet.

*Petal claw.*—

*Form.*—The claw is considered to have a triangular form, narrower at the base.

*Length.*—Between 2.0 and 2.5 millimeters.

*Width.*—Approximately 1.5 millimeters.

*Color.*—Dark pink (RHS Red Purple 63 A).

*Petal margins.*—Generally considered moderately wavy, sinuate.

*Petal apex.*—

*Generally.*—The petal apices are generally wide-dome shaped.

*Flower pedicel.*—

*Length.*—Considered medium and having an average length of approximately 1.5 to 2.0 millimeters.

*Diameter.*—Considered average, approximately 1.0 to 1.5 millimeters.

*Color.*—Green (RHS Yellow Green 145 A).

*Calyx.*—

*Internal surface texture.*—Smooth and glabrous.

*Color.*—At the stage F of blooming, when the flower is open, the inner surface of the calyx, or flower receptacle, is matt and considered yellow green (RHS Greyed Orange 163 B). The outer surface of the calyx is considered of purple-brown color (RHS Greyed Purple 187 A or RHS Greyed Purple 187 B).

*Sepals.*—

*Sepal count.*—Usually five.

*Surface texture.*—The outer surface has a fine pubescent texture.

*Size.*—Medium.

*Form.*—Conic with a round tip.

*Length.*—Approximately 5.0 to 7.0 millimeters.

*Width.*—Approximately 4.0 to 6.0 millimeters.

*Color.*—At the stage F of blooming, the upper surface of the sepals is considered of purple-brown color (RHS Greyed Purple 187 A or RHS Greyed Purple 187 B). The lower surface of the sepals is considered greenish or greenish yellow (RHS Yellow Green 148 A to RHS Yellow Green 148 B).

*Average number of stamens per flower.*—Approximately 38 to 42 stamens per flower.

*Anthers.*—

*Size.*—Considered medium.

*Shape.*—Cordate.

*Color.*—Anthers are colored with red color (RHS Orange Red Group N34 A).

*Pollen production.*—Pollen is abundant, and has a yellow color (RHS Yellow 13 A) which may evolve with maturity. The present variety is considered auto-fertile (self-pollinating).

*Filaments.*—

*Size.*—Medium length, between 16.0 and 20.0 millimeters in length. Filaments length is generally higher than the pistil's length, or equal to the pistil's length (considered without the ovary).

*Color.*—Considered white (RHS White 55 D) and becoming pink (RHS Red Purple 63 C to RHS Red Purple 63 D) during the blooming.

*Pistil.*—

*Number.*—Usually 1.

*Generally.*—Average in size.

*Length.*—Approximately 19.0 to 22.0 millimeters including the ovary.

*Color.*—Considered a very pale green (RHS Yellow Green 150 C).

*Stigma.*—Approximately 1.0 millimeter in diameter, with a light green to yellow color (RHS Yellow Green 154 A).

*Ovary.*—Approximately 2.5 to 3.0 millimeters in height. The diameter of the ovary is about 1.5 to 2.5 millimeters. The color is considered light green (RHS Yellow Green 145 B).

*Pubescence.*—Present.

Fruit:

*Maturity when described.*—Firm in ripe conditions (shipping ripe).

*Date of first picking.*—Aug. 2, 2015.

*Date of last picking.*—The date of harvest varies slightly with the prevailing climatic conditions. The 'PBRO15170' variety has a medium date of picking, and a grouped maturity. The maturity is grouped within 6 to 8 days and the harvest is generally performed in two runs. Last known picking times carry on from Aug. 2 to Aug. 9, 2015, then from Aug. 2 to Aug. 9, 2016 and then from Jul. 30 to Aug. 4, 2017.

*Size.*—

*Generally.*—Homogeneous in size 2A or 3A. Considered large.

*Average cheek diameter.*—Approximately 71.0 to 80.0 millimeters.

*Average axial diameter.*—Approximately 69.0 to 73.0 millimeters.

*Typical weight.*—Generally about 250.0 grams. This characteristic is high dependent upon the prevailing cultural practices, and therefore is not particularly distinctive of the variety.

*Fruit form.*—

*Generally.*—Round. The fruit is generally slightly asymmetrical, viewed from the suture's plane.

*Suture.*—

*Fruit suture.*—Flared and slightly marked, extending from the base to the apex. No apparent callousing or stitching exists along the suture line. Not pointed.

*Color.*—The suture has generally a similar color to the whole fruit color, a luminous purple red (RHS Greyed Purple N186 B or RHS Greyed Purple 187 A).

*Mucron.*—Absent.

*Apex.*—Non-prominent, small and generally slightly depressed.

*Base.*—Flared, shallow.

*Stem cavity.*—Average depth of the stem cavity is about 15.0 to 18.0 millimeters. Average width is about 22.0 to 25.0 millimeters.

*Fruit skin.*—

*Thickness.*—Considered medium thick and strong, and the adherence of skin to flesh is medium.

*Texture.*—Fine pubescence, almost non-existent.

*Taste.*—Semi-sweet.

*Tendency to crack.*—None observed.

*Lenticels.*—No lenticels.

*Color.*—

*Blush color.*—This blush color is an homogenous purple red (RHS Greyed Purple N186 B or RHS Greyed Purple 187 A). The purple red blush covers approximately 75 to 85% of the fruit skin surface on a washed red or pink red background (RHS Greyed Red 180 A to RHS Greyed Red 180 B) on approximately 15 to 25% of the fruit skin surface. The percentage of the blush on the fruit skin surface can vary, and is generally dependant upon the prevailing conditions under which the fruit was grown.

*Ground color.*—The ground color covers approximately 15 to 25% of the fruit skin surface, and is considered washed red or pink red background (RHS Greyed Red 180 A to RHS Greyed Red 180 B).

*Fruit stem.*—Medium in length, approximately 7.0 to 8.0 millimeters.

*Diameter.*—Approximately 4.0 to 5.0 millimeters.

*Color.*—Pale green (RHS Yellow Green 145 A).

*Flesh.*—

*Ripens.*—Very homogenously, slowly. The flesh has a long shelf life.

*Texture.*—Firm, crunchy, melting, juicy at harvest maturity stage.

*Fibers.*—Not fibrous.

*Aroma.*—Pronounced.

*Eating quality.*—Considered very good, aromatic, with a high level of sugars but semi-sweet due to acidity level between 6 and 9 meq/100 mL.

*Flavor.*—Considered semi-sweet. The Brix is generally around 15.

*Juice.*—Medium juicy at complete maturity.

*Brix.*—Generally 15.0 degrees. This characteristic varies slightly with the number of fruit per tree; prevailing cultural practices; and the surrounding climatic conditions.

*Flesh color.*—White flesh (RHS White 155 D) usually with a red pigmentation (RHS Red 53 C or RHS Red 53 D) into the stone cavity and around the stone cavity, more or less in a stared-shape over 8.0 to 10.0 mm around the stone.

Stone:

*Type.*—Semi-Clingstone, more or less adherent depending on the fruit maturity.

*Size.*—Considered medium for the variety. The stone size varies significantly depending upon the tree vigor, crop load and prevailing growing conditions.

*Length.*—Approximately 28.0 to 30.0 millimeters.

*Width.*—Approximately 20.0 to 23.0 millimeters.

*Diameter.*—Approximately 16.0 to 17.0 millimeters.

*Form.*—Obovate.

*Base.*—Oblique.

*Apex.*—

*Shape.*—The stone apex is short and pointed.

*Stone cavity.*—Considered medium in size, with an obovate-form and dimensions corresponding to the stone's dimensions.

*Stone surface.*—

*Surface texture.*—The pit is transversely furrowed on its entire surface. Furrows are more pronounced toward the apex. The stone is pitted toward the base. Relief is prominent generally and present basally.

*Ridges.*—The surface texture is generally characterized by more prominent ridges along the ventral edges and is more prominent at the apical tip.

*Ventral edge.*—

*Width.*—Considered small, and having a depth of approximately 1.5 millimeters at mid-suture.

*Dorsal edge.*—

*Shape.*—Grooved.

*Stone color.*—The color of the dry stone is generally considered light orange brown (RHS Greyed Orange 164 B to RHS Greyed Orange 164 C).

*Tendency to split.*—Splitting is absent.

*Kernel.*—

*Size.*—The kernel is considered medium.

*Length.*—Approximately 14.0 to 15.0 millimeters.

*Width.*—Approximately 8.0 to 9.0 millimeters.

*Thickness.*—Approximately 3.0 to 4.0 millimeters.

*Form.*—Considered elliptic.

*Pellicle.*—The pellicle of the kernel has a short pubescence.

*Color.*—The kernel skin is light orange-brown colored (RHS Greyed Orange N 167 A). The almond, which is the seed of the kernel, is white (RHS White 155 D) and has a sweet tasting. The kernel and its embryo are mature at the time of fruit maturity.

*Use.*—The subject variety 'PBRO15170' is considered to be a white peach tree of the medium season of maturity, and which produces fruits that are considered firm, attractively colored with a luminous purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long-distance shipping.

*Keeping quality.*—Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.

*Shipping quality.*—Considered very good. The fruit of the new white peach variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

*Resistance to insects and disease.*—No particular susceptibilities were noted. The present variety is not sensitive to powdery mildew, or conservation diseases and decay due to its thick and strong skin.

Although the new variety of peach tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of white peach tree as illustrated and described, characterized by its resistance to main pests and diseases, its, fruits with high eating quality and very long shelf life without alteration before and after harvesting, with a semi-sweet white flesh, with a red pigmentation into the stone cavity and around the cavity, and an attractive luminous and homogenous skin with a high percentage of purple red blush on skin surface, on a pink red background.

* * * * *